(12) United States Patent
Vogel et al.

(10) Patent No.: US 10,292,607 B2
(45) Date of Patent: May 21, 2019

(54) SENSOR DATA TRANSMISSIONS

(71) Applicant: Intel Corporation, Santa Clara, CA (US)

(72) Inventors: Brian K. Vogel, Santa Clara, CA (US); John C. Wei, Saratoga, CA (US); Fai Angus Yeung, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 313 days.

(21) Appl. No.: 14/670,326

(22) Filed: Mar. 26, 2015

(65) Prior Publication Data
US 2016/0278648 A1  Sep. 29, 2016

(51) Int. Cl.
*A61B 5/02* (2006.01)
*A61B 5/024* (2006.01)
(Continued)

(52) U.S. Cl.
CPC ........ *A61B 5/02438* (2013.01); *A61B 5/6817* (2013.01); *A61B 5/6898* (2013.01);
(Continued)

(58) Field of Classification Search
CPC .............. A61B 5/0006; A61B 5/02438; A61B 2560/0468; A61B 2560/0431; A61B 5/6817; A61B 5/6898; A61B 5/72; H04L 5/0053; H04M 1/72527; H04M 2250/12; Y02D 70/00; Y02D 70/1262; Y02D 70/142; Y02D 70/144; Y02D 70/146; Y02D 70/164; Y02D 70/26
See application file for complete search history.

(56) References Cited

U.S. PATENT DOCUMENTS 5,919,141 A * 7/1999 Money ............... A61B 5/02055
600/483
8,157,730 B2  4/2012  LeBoeuf et al.
(Continued)

FOREIGN PATENT DOCUMENTS

EP    1922989    5/2008
TW    I362923 B1  5/2012
(Continued)

OTHER PUBLICATIONS

PCT Application No. PCT/US2016/019940 filed Feb. 26, 2016; Intel Corporation; International Search Report dated Jun. 8, 2016.
(Continued)

*Primary Examiner* — Amanda K Hulbert
(74) *Attorney, Agent, or Firm* — Thorpe North and Western, LLP; David W. Osborne

(57) ABSTRACT

Technology for a wearable heart rate monitoring device is disclosed. The wearable heart rate monitoring device can include a heart rate sensor operable to collect sensor data, a modulator operable to generate a modulated signal that includes the sensor data, a housing configured to engage a body feature or surface in a manner that allows for heart rate detection, and a communication module configured to transmit the sensor data in the modulated signal to a mobile computing device via a wired connection that is power limited. The mobile computing device is typically configured to demodulate the modulated signal in order to extract the sensor data.

19 Claims, 8 Drawing Sheets

(51) Int. Cl.
*A61B 5/00* (2006.01)
*H04L 5/00* (2006.01)
*H04M 1/725* (2006.01)

(52) U.S. Cl.
CPC .............. *A61B 5/72* (2013.01); *H04L 5/0053* (2013.01); *A61B 2560/0431* (2013.01); *H04M 1/72527* (2013.01); *H04M 2250/12* (2013.01); *Y02D 70/00* (2018.01); *Y02D 70/1262* (2018.01); *Y02D 70/142* (2018.01); *Y02D 70/144* (2018.01); *Y02D 70/146* (2018.01); *Y02D 70/164* (2018.01); *Y02D 70/26* (2018.01)

(56) References Cited

U.S. PATENT DOCUMENTS

| | | | |
|---|---|---|---|
| 2004/0059205 A1 | 3/2004 | Carlson et al. | |
| 2007/0249946 A1* | 10/2007 | Kumar | A61B 5/0006 600/515 |
| 2009/0105548 A1* | 4/2009 | Bart | A61B 5/02438 600/300 |
| 2010/0189268 A1 | 7/2010 | Haartsen et al. | |
| 2011/0301439 A1 | 12/2011 | Albert et al. | |
| 2013/0343585 A1 | 12/2013 | Bennett et al. | |
| 2014/0161300 A1 | 6/2014 | Prest et al. | |
| 2015/0031967 A1 | 1/2015 | LeBoeuf et al. | |
| 2016/0278647 A1 | 9/2016 | Vogel et al. | |

FOREIGN PATENT DOCUMENTS

| | | | |
|---|---|---|---|
| TW | M489624 U | 11/2014 | |
| TW | M493490 U | 1/2015 | |
| WO | WO2014/121837 | 8/2014 | |
| WO | WO 2015177787 A1 * | 11/2015 | ............... G06K 9/00 |

OTHER PUBLICATIONS

PCT Application No. PCT/US2016/019957 filed Feb. 26, 2016; Intel Corporation; International Search Report dated Jun. 8, 2016.
Taiwan IPO Search Report issued with foreign office action dated May 11, 2018, in TW Application No. 105105326, filed Feb. 23, 2016; 2 pages; [English translation included].

* cited by examiner

SENSOR DATA TRANSMISSIONS

TECHNICAL FIELD

Technology described herein relates generally to wearable electronic devices.

BACKGROUND

The popularity of wearable technology, such as smart watches and smart eyewear, has grown in recent years. Wearable technology can include clothing or accessories that incorporate computer and electronic technologies. Wearable technology can perform a variety of functions that are beneficial to a user, in addition to being aesthetically pleasing. For example, wearable technology can provide health monitoring and health metrics, music listening, global positioning system (GPS) capabilities, activity tracking, telephony services, and Internet browsing, for the user that is wearing the wearable technology.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein.

Figure 1:
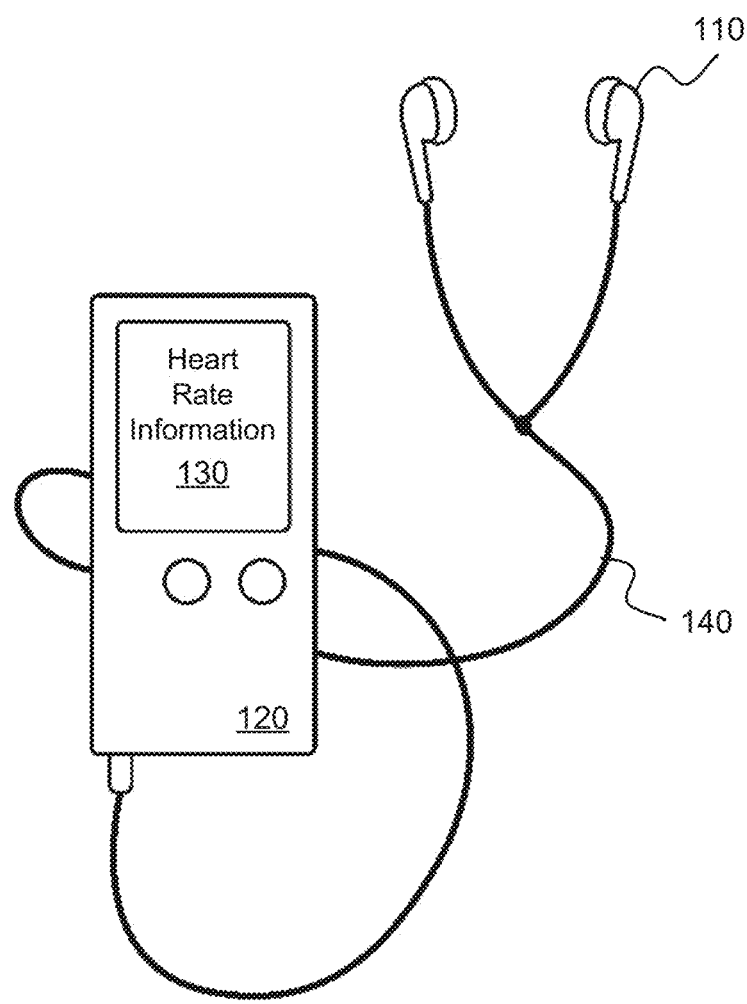
FIG. 1 illustrates a heart rate monitoring headphone communicating heart rate information to a mobile device in accordance with an example.

Reference will now be made to the exemplary embodiments illustrated, and specific language will be used herein to describe the same. It will nevertheless be understood that no limitation of the scope of the disclosure is thereby intended.

DETAILED DESCRIPTION

Before the present invention is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics may be combined in any suitable manner in one or more embodiments. In the following description, numerous specific details are provided, such as examples of layouts, distances, network examples, etc., to provide a thorough understanding of various invention embodiments. One skilled in the relevant art will recognize, however, that such detailed embodiments do not limit the overall inventive concepts articulated herein, but are merely representative thereof.

Example Embodiments

An initial overview of technology embodiments is provided below and then specific technology embodiments are described in further detail later. This initial summary is intended to aid readers in understanding the technology more quickly, but is not intended to identify key or essential technological features nor is it intended to limit the scope of the claimed subject matter. Unless defined otherwise, all technical and scientific terms used herein have the same meaning as commonly understood by one of ordinary skill in the art to which this disclosure belongs.

Reference throughout this specification to "an example" means that a particular feature, structure, or characteristic described in connection with the example is included in at least one invention embodiment. Thus, appearances of the phrase "in an example" in various places throughout this specification are not necessarily all referring to the same embodiment.

As used in this specification and the appended claims, the singular forms "a," "an" and "the" include plural referents unless the context clearly dictates otherwise. Thus, for example, reference to "a cable" includes a plurality of such cables.

In this specification, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "low power," "limited power," and the like refer to an amount of power that is typically provided by an audio jack on a mobile device, in order to suitably and sufficiently power audio signals to headphones or earbuds, such as music or other dialog. In one embodiment, "low power" may refer to an amount of power that is less than 2 mW. In another embodiment, the amount of power can be less than 1.5 mW. In a further embodiment, the amount of power can be less than 1 mW.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for the exact number or numerical range without the term "about". For example, for the sake of convenience and brevity, a numerical range of "about 50 angstroms to about 80 angstroms" should also be understood to provide support for the range of "50 angstroms to 80 angstroms."

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and invention examples may be referred to herein along with alternatives for the various components thereof. It is understood that such embodiments, examples, and alternatives are not to be construed as defacto equivalents of one another, but are to be considered as separate and autonomous representations of various invention embodiments.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, in reciting the range of "about 1 to about 5," support is given for all sub-ranges within the range such as from 1-3, from 2-4, from 3.5-4.5 and from 3-5, etc., as well as the individual numbers 1, 2, 3, 4, and 5 and further including portions or fractions thereof such as 2.5, 3.6, 4.8, 1¾, 3¼, and 4½.

A technology is described for detecting heart rate data in a subject and reporting said heart rate using a computing device, such as a mobile computing device, or simply "mobile device", to which a heart rate sensor or monitoring device is wiredly coupled or connected (i.e. connected with a cable or a wire). In a related aspect, a technology for demodulating sensor data received at a mobile device from a heart rate monitoring device is provided. In one embodiment, the heart rate monitoring device can be earbud speakers with heart rate monitoring functionality. The heart rate monitoring device can collect sensor data (e.g., heart rate information) via heart rate sensors in a user's ear. The sensor data can be modulated and sent over a microphone line to a mobile device. The sensor data can include a series of data samples that are modulated using one of two frequency tones (e.g., 12 kHz or 18 kHz). The mobile computing device can demodulate the sensor data and display the sensor data to the user. In one example, the mobile computing device can effectively demodulate the sensor data in the presence of noise and clock drift. In order to demodulate the signal data, the mobile computing device can select a sampling rate at which to select data samples from the modulated sensor data. The sampling rate can be selected to mitigate the clock drift. The mobile computing device can select data samples from the series of data samples in accordance with the sampling rate. In one example, the mobile computing device can select one data sample out of approximately every seven data samples. A discrete data value (e.g., a "0" or a "1") can be determined for each data sample that is selected. The discrete data value can be determined by comparing the selected sample to a defined threshold. The discrete data values can represent demodulated digital sensor data. The sensor data can be converted into heart rate information and displayed to the user via a display on the mobile device.

One example of wearable devices (i.e. wearable sensor devices) includes a heart rate monitoring device. The heart rate monitoring device can take the form of smart earbuds (or smart headphones) with heart rate monitoring functionality. The heart rate monitoring functionality can be provided from in-ear heart rate sensors that are embedded in the earbuds. The heart rate monitoring device can be inserted into the user's ear and collect sensor data (e.g., heart rate information) for the user using the heart rate sensors. The heart rate monitoring device can be connected to a mobile device (e.g., a mobile computing device such as a phone or tablet) via a wired connection. The wired connection can include a microphone line (i.e. audio-in line that carries an audio signal from a microphone to the mobile device) or a headphone line (i.e. audio-out line that carries an audio signal from the mobile device to the headphone speakers) or both. The microphone line and headphone line can also be referred to herein generally as "cables," "lines," "wires," or "wired connection(s)" that connect the heart rate monitoring device to the mobile device. In some aspects, the microphone and headphone lines can simply be referred to either collectively or individually as "audio cable(s), or "audio line(s)". The heart rate information can be transmitted from the heart rate monitoring device to the mobile device via the audio cable(s). The heart rate information can be displayed to the user via a mobile application that is running on the mobile device. In addition, the heart rate information can be displayed whether or not audio is being provided by the speakers in the heart rate monitoring device.

FIG. 1 illustrates an exemplary heart rate monitoring device 110 communicating heart rate information 130 to a mobile device 120. The heart rate monitoring device 110 can also be referred to as smart earbuds, or earbuds, that are capable of detecting heart rate information 130. The heart rate monitoring device 110 can be inserted within a user's ear. The heart rate monitoring device 110 can include a heart rate sensor (not shown in FIG. 1) that collects the heart rate information 130 and sends the heart rate information 130 to the mobile device 120. In one example, the heart rate information 130 can be sent via a wired connection between the heart rate monitoring device 110 and the mobile device 120. The wired connection can be an audio line 140 such as a microphone line or a headphone line. The mobile device 120 can display the heart rate information 130 for the mobile device's user.

In one configuration, the heart rate monitoring device 110 can include other sensors, such as an accelerometer, gyroscope, proximity sensor, temperature sensor, etc. The heart rate monitoring device 110 can send sensor data (e.g., accelerometer data, gyroscope data, proximity data, and temperature data) to the mobile device 120 via the wired connection between the heart rate monitoring device 110 and the mobile device 120.

While a battery can be used to power the heart rate monitoring device 110, in one example, the heart rate monitoring device 110 does not include a battery because the necessary power for operating the heart rate monitoring device 110 can be harvested from the audio jack (i.e. jack into which the audio cable plugs) on the mobile device 120. Hence, the mobile device becomes the power source for or "powers" the heart rate monitoring device. In another example, the heart rate monitoring device 110 can be limited to operating under a maximum power of about 1 milliwatt (mW) due to the maximum amount of power that is provided from the audio jack of typical smart phones. The power used to power the headphone speakers and/or microphone can be referred to as "mic bias power". Therefore, in some embodiments the amount of power for the heart rate sensors in the heart rate monitoring device 110 (as well as other sensors) can be limited to about 1 mW. In addition, the approximately 1 mW of power can be used to power a microcontroller in the heart rate monitoring device 110. The microcontroller can send the collected sensor data over the audio line 140 to the mobile device 120.

In one example, the microcontroller can read the sensor data (e.g., the heart rate information 130) and modulate the sensor data into some waveform that can be sent to the mobile device 120 over the audio line 140. The mobile device 120 can include a demodulator that demodulates the waveform and extracts the sensor data. In other words, in one embodiment modulated signals containing the sensor data can be demodulated at the mobile device 120 in order to extract the sensor data. However, in some cases, the modulated waveform can experience noise or cross-talk due to audio signals (e.g., music or voice) that are sent to the speakers in the heart rate monitoring device 110. The noise can result as the audio signals are traveling from the mobile device 120 to the heart rate monitoring device 110 via the audio line 140 and the modulated waveform (i.e., the modulated sensor data) is traveling from the heart rate monitoring device 110 to the mobile device 120 via the audio line 140.

In one example, the noise can be caused by electrical coupling in the audio line 140 that connects the mobile device 120 and the heart rate monitoring device 110. The electrical coupling can occur due to the closeness of the wires in the audio line 140, for example the closeness of the microphone line and the headphone line. The electrical coupling can cause some of the audio signals sent to the speakers to be picked up in the microphone line, thereby causing the noise in the modulated waveform (i.e., the modulated sensor data). Since the modulated waveform is generally of low energy, increased noise in the modulated waveform can result in increased difficulties when it is demodulated at the mobile device 120. The amount of electrical coupling can also vary depending on the type of mobile device.

In one example, the modulated sensor data is sent from the heart rate monitoring device 110 to the mobile device 120 through the audio line that is used for the microphone (i.e. the microphone line). In other words, the microphone sits in line on the audio cord. Either the microphone or the heart rate functionality can be used at a given time. In addition to powering the headphone speakers, the approximately 1 mW of power from the headphone or microphone jack is also used to power the microphone and the heart rate monitoring device. If the microphone is not toggled off when the heart rate information 130 is being sent to the mobile device, the amount of power required to communicate both the microphone data and the sensor data can exceed the approximately 1 mW of available power. Therefore, in some embodiments, the heart rate monitoring device 110 can include a switch for the user to manually switch the device to heart rate mode or microphone mode. In other embodiments, the switch can be automatically operated to toggle off the microphone when the heart rate monitoring device is activated or vice versa. In such case, the user may assign a priority of operation to either the heart rate monitoring device or the microphone using software on mobile device. In some aspects, the priority can be assigned depending on other programs that are in operation on the mobile device. For example, when software meant for exercise tracking is operational, the heart rate monitoring device may be automatically switched on and the microphone switched off. Alternatively, when a phone call is received, the heart rate monitoring device may be switched off and the microphone switched on. In some aspects, the microphone can be given priority over the heart rate monitoring device so that when the heart rate monitoring device is operational and a phone call is received, that the microphone is automatically switched on and the heart rate monitoring device is switched off. Once the phone call is ended, the microphone can be switched off and the heart rate monitoring device can be switched back on.

When the heart rate mode is activated, the heart rate monitoring device 110 can send the heart rate information 130 on the microphone line instead of the microphone data, and vice versa. However, if the amount of available power is sufficient to send both types of data simultaneously, then the microphone data generally does not cause noise for the sensor data since the sensor data is modulated using higher frequencies as compared to the microphone data.

In one configuration, data from the heart rate sensors in the heart rate monitoring device 110 can be digitized by an analog-to-digital converter (ADC) at a sampling rate of approximately 25 hertz (Hz). Thus, approximately 25 samples are collected per second. For each sample, the microcontroller in the heart rate monitoring device 110 can construct a data packet containing the digitized sensor values and other information, such as a packet header, packet footer, product identifier code, and an error detection code (e.g., a cyclic redundancy check). The data packet can be modulated using binary frequency-shift keying (BFSK). The BFSK frequencies can be chosen to be close to a maximum frequency level supported by the mobile device 120 (e.g., 12-18 kHz), such that the BFSK frequencies are mostly inaudible and can reduce cross talk interference from the audio signals that are played through the speakers of the heart rate monitoring device 110.

The sensor data (e.g., the heart rate information 130) collected at the heart rate monitoring device 110 can be converted into a binary sequence of 0s and 1s. The sensor data can be demodulated using the two frequency tones. In one example, a first tone can be 12 kHz and a second tone can be 18 kHz. Frequency tones in the range of 12-18 kHz are generally high frequency and unable to be heard as they are on the upper end of the human hearing range. Each binary value in the sensor data can be modulated using one of the two frequency tones. For example, a "0" can be turned into a 12 kHz tone and a "1" can be turned into an 18 kHz tone. Therefore, the modulated signal (i.e. the modulated sensor data) that travels from the heart rate monitoring device 110 to the mobile device 120 can alternate between, for example, 12 kHz and 18 kHz.

The mobile device 120 can include a demodulator to demodulate the modulated signal (i.e., the alternations between 12 kHz and 18 kHz) received from the heart rate monitoring device 110. The mobile device 120 can determine that the signals modulated at 12 kHz correspond to the binary value of "0" and that the signals modulated at 18 kHz correspond to the binary value of "1". In order for the demodulator to decode the modulated signals accurately, the demodulator can know a length of the transmit intervals (or symbol intervals). In other words, the demodulator can know how many 12 kHz signal values or 18 kHz signal values are transmitted for a single symbol (i.e., a "0" or a "1"), respectively. The signal values can also be referred to as samples. If the heart rate monitoring device 110 wishes to send a sequence of several consecutive 1s, then the consecutive 1s are modulated at the 18 kHz tone for a defined duration (i.e., for a defined number of samples). The demodulator at the mobile device 120 can receive the duration of 18 kHz signal values, but if the demodulator does not know how long it takes to transmit one symbol, then the demodulator does not know how many values of 1 are included in the duration of 18 kHz signal values.

In one configuration, each packet of data received from the heart rate monitoring device 110 at the mobile device 120 can contain 74 symbols (i.e., a set of 74 "1s" and/or "0s"). Each symbol can last approximately 0.16 milliseconds (ms). Therefore, one packet of data can be 11.84 ms in duration. The demodulator in the mobile device 120 can collect audio samples at the rate of 44,100 samples per second (or 44.1 samples/ms). Therefore, the data packet has 522.144 samples (i.e., 44.1 samples/ms×11.84 ms), and each symbol in the data packet has 7.056 samples. Therefore, if the heart rate monitoring device 110 wants to transmit a "0" to the demodulator in the mobile device 120, it takes approximately 7 samples at the 12 kHz tone to convey the "0". Similarly, if the heart rate monitoring device 110 wants to transmit a "1" to the demodulator in the mobile device 120, it takes approximately 7 samples at the 18 kHz tone to convey the "1". Therefore, when the modulated signal received at the demodulator stays at 12 kHz for approximately 7 samples, then this indicates a binary value of "0", and when the modulated signal received at the demodulator stays at 18 kHz for approximately 7 samples, then this indicates a binary value of "1". The binary values of "0" and "1" that are extracted from the modulated signal can represent the sensor data (e.g., the heart rate information 130).

In one example, the microprocessor included in the heart rate monitoring device 110 can include a mixed signal microprocessor. The microprocessor can generate approximately 25 packets of data a second. The 25 packets of data include the sensor data collected by the heart rate sensors in the heart rate monitoring device 110. Each of the 25 packets of data can contain 74 symbols, which results in approximately 13,053.6 samples (i.e., 25×74×7.056) being transmitted per second from the heart rate monitoring device 110 to the mobile device 120. The demodulator on the mobile device 120 can collect the samples at a rate of 44,100 samples per second. The demodulator can perform a data filtering, such that the number of samples per a given second is substantially the same as the number of samples provided by the microprocessor in the heart rate monitoring device 110. The demodulator can decode this filtered packet of data by performing down sampling. The demodulator can have an estimate of the start of the packet, and then the demodulator selects a single sample per symbol length. In other words, the demodulator can select a single sample every 7.056 samples or approximately every 0.16 ms. The value of 7.056 samples has to be fairly precise in order to decode the samples accurately. Based on the frequency tone associated with each sample (i.e., 12 kHz or 18 kHz), the demodulator can determine the binary value (i.e., "0" or "1"). A plurality of binary values can be converted to sensor data at the mobile device 120 and then displayed to the mobile device's user.

In ideal circumstances, the demodulator can select one sample per symbol length (e.g., 7.056 samples), wherein the symbol length remains stable over a period of time. However, clock drift between the microprocessor's clock and the mobile device's clock can alter the symbol length. In one example, the microprocessor in the heart rate monitoring device 110 can be more susceptible to clock drift due to the power constraints of the heart rate monitoring device 110. In other words, a less accurate microprocessor may have to be used in order to comply with the 1 mW power constraint of the audio jack, which can result in an increased amount of clock drift between the microprocessor in the heart rate monitoring device 110 and the mobile device 120. The increased clock drift can lead to variation in the modulated frequencies as well as the packet data rate.

If the microprocessor of the heart rate monitoring device 110 has A % drift against the mobile device's clock, then the same packet of data lasts 11.84×(1+A %) ms from the mobile device's perspective, resulting in 11.84×(1+A %)×44.1=522.144×(1+A %) samples per packet of data. In this case, "A" can be a positive or negative integer and up to ±3.5. A negative "A" value leads to a loss of samples. If "A" is positive, there is a risk that the same symbol could be down sampled twice by the mobile device 120. If "A" is negative, then there is a risk that some symbols are entirely emitted during the down sampling. Either way, errors can result due to the clock drift.

In one embodiment, the technology herein describes techniques for demodulating signals in the presence of clock drift. In addition, the technique describes demodulating signals in the presence of interference noise (or cross talk) due to electrical coupling in the audio line, particularly the microphone line, as described earlier. The techniques can adaptively and efficiently estimate and compensate for clock drift, we well as providing decision thresholds for optimal decoding when a relative scaling of the two frequency shift keying (FSK) components are unknown.

Figure 2:
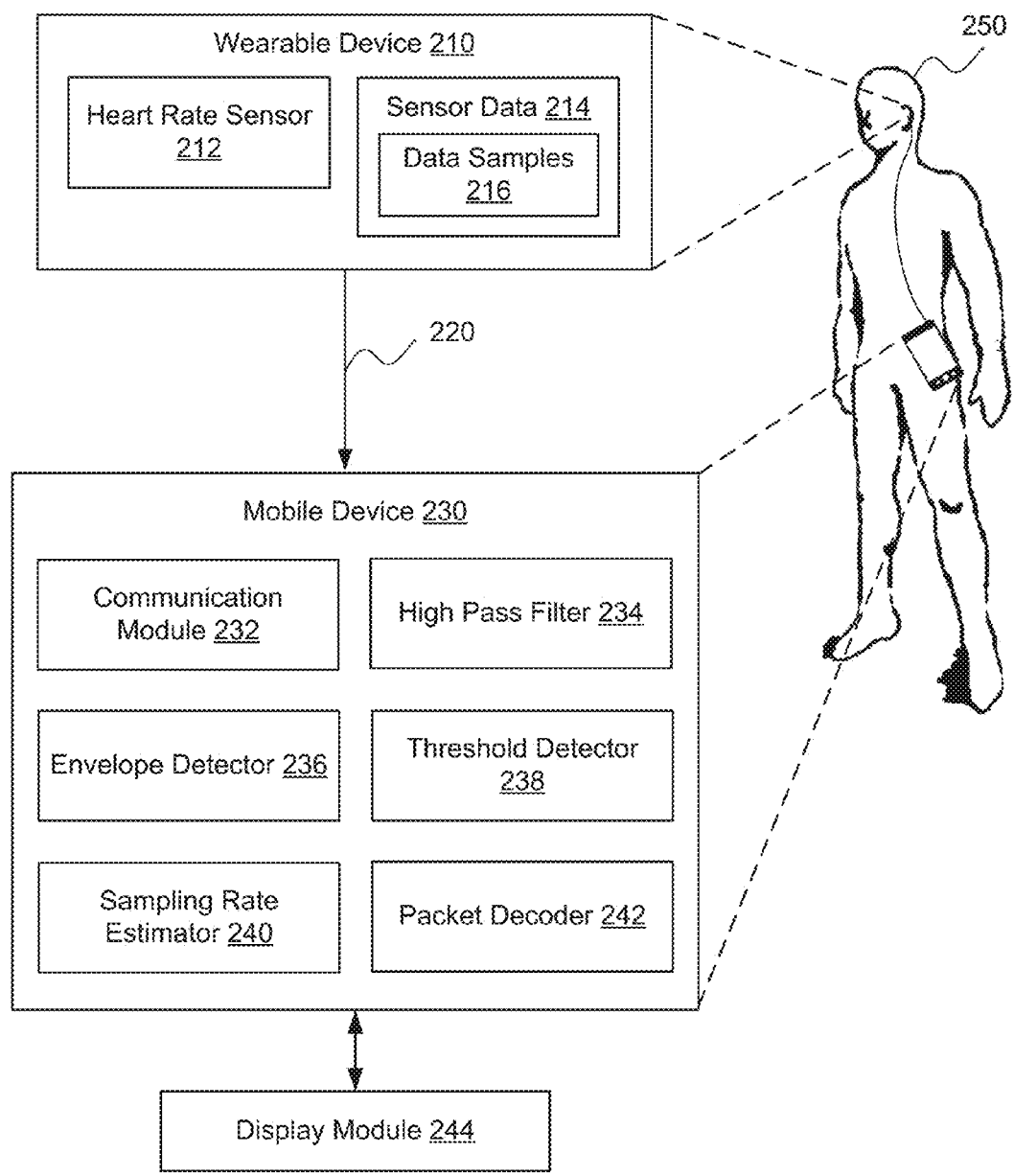
FIG. 2 illustrates a system and related operations for demodulating sensor data received at a mobile device from a wearable device in accordance with an example.

FIG. 2 illustrates an exemplary system and related operations for demodulating sensor data 214 received at a computing device or mobile computing device 230 from a wearable sensor device 210. The wearable device (i.e. wearable sensor device) 210 can include a heart rate monitoring device. In one embodiment, the heart rate monitoring device can be earbud speakers with heart rate functionality. In other words, the wearable device 210 can be inserted in a user's ear in order to collect heart rate information. In order to transmit the heart rate information from the wearable device 210 to the mobile device, a modulation and demodulation technique can be used. Modulation is the process of conveying a message signal, such as an analog audio signal, in another signal (e.g., a carrier signal) that can be physically transmitted. During modulation, digital information can be transmitted through discrete frequency changes in the carrier signal. Demodulation is the process of extracting the original information-bearing signal from the carrier signal. In this example, the sensor data 214 can be transmitted from the wearable device 210 to the mobile device 230 via an audio line, such as microphone line 220.

As mentioned, the sensor data 214 (e.g., the heart rate information) can include a plurality of data samples 216 (e.g., audio samples) that are digitized into binary sensor values. The binary values can be modulated using frequency-shift keying (BFSK). In BFSK, a pair of discrete frequencies can be used to transmit binary information (i.e., 0s and 1s). The binary values can be modulated at the wearable device 210 using two BFSK frequency tones. For example, a "0" can be modulated using a 12 kHz tone and a "1" can be modulated using a 18 kHz tone. Therefore, the modulated signal can be at 12 kHz or 18 kHz for certain periods of time depending on the sensor data that is modulated. The 12 kHz and 18 kHz frequencies are high frequency tones that are higher than frequencies generally used for music and audio.

The modulated signal can be an analog signal that is received at the mobile device 230 via a communication module 232, but in order to extract the sensor data 214 from the modulated signal (i.e., demodulate the modulated signal), the mobile device 230 has to perform a number of steps. The modulated signal (i.e., the alternating 12 kHz and 18 kHz tones) can be provided to a high pass filter 234. The high pass filter 234 can let through signals that are above a defined frequency level, but does not let through signals that are below the defined frequency level. In other words, the high pass filter 234 can remove frequency components other than those in between the two BFSK frequency tones. In one example, the high pass filter 234 can include a finite impulse response (FIR) filter with 7-25 taps depending on implementation, as well as a cutoff frequency in the range of 9-10 kHz. The high pass filter 234 can filter out lower frequency signals, which can include music or audio. As a result, the high pass filter 234 can remove some of the noise interference (or cross talk) included in the modulated signal. However, some music can have high frequency tones at certain times, so the high pass filter 234 may not completely remove the noise interference from the modulated signal.

The high pass filtered signal (i.e., the 12 kHz and 18 kHz signals) can be provided to an envelope detector 236. The envelope detector 236 can take a high frequency signal as input and provide an output which is an envelope of the original input signal. The envelope detector 236 can output two signals $r_1$ and $r_2$. The two signal outputs can correspond to two filters that are centered at the two frequencies—12 kHz and 18 kHz. In one example, $r_1$ can correspond to 12 kHz and $r_2$ can correspond to 18 kHz. Depending on the frequency of the high pass filtered signal, either the $r_1$ component or the $r_2$ component can be larger. For example, if the filtered signal is at 12 kHz, then $r_1$ has a frequency greater than zero and $r_2$ has a frequency that is approximately zero. If the filtered signal is at 18 kHz, then $r_1$ has a frequency that is approximately zero and $r_2$ has a frequency that is greater than zero. Therefore, either one of $r_1$ or $r_2$ can have a stronger signal as compared to the other, depending on whether the filtered signal is at 12 kHz or 18 kHz.

In addition, the first signal ($r_1$) and the second signal ($r_2$) can be associated with a particular data sample 216 in the modulated sensor data. As a non-limiting example, 7 consecutive data samples of the filtered signal can each correspond to $r_1$ being zero and $r_2$ being greater than zero, the next 21 consecutive data samples of the filtered signal can each correspond to $r_2$ being greater than zero and $r_2$ being zero, the next 14 consecutive data samples of the filtered signal can each correspond to $r_1$ being zero and $r_2$ being greater than zero, and so on.

In one example, the first signal ($r_1$) and the second signal ($r_2$) of the data sample 216 is represented by $r_1=\sqrt{\cos(2\pi f_c t)^2+\sin(2\pi f_c t)^2}$ and $r_2=\sqrt{\cos(2\pi(f_c+\Delta F)t)^2+\sin(2\pi(f_c+\Delta F)t)^2}$, respectively, wherein $f_c$ is a signal frequency, t is a period of time, and $\Delta F$ is a frequency offset. The signals $r_1$ and $r_2$ can be referred to as envelope signals. The values of $f_c$ and $\Delta F$ can be chosen, such that r1 and $r_2$ are orthogonal over a symbol interval T. In one example, $T=2/f_c$, $f_c=12,000$ Hz, and $\Delta F=6000$ Hz. Due to clock drift, these values can vary by several percent.

In a traditional square law detector (or envelope detector 236), a difference signal (d) can be computed from $d=r_1-r_2$. The difference signal (d) can be computed at selected sampling locations (or sampling time instances). The selected sampling locations can be determined based on a sampling rate. For example, the difference signal (d) can be computed approximately every 7 samples within the series of data samples 216 that are contained in the sensor data 214. In other words, one out of every 7 samples can be selected, and the difference signal (d) can be calculated for that one sample. If d>0, then that particular data sample 216 corresponds to a binary value of 1, and if d<0, then that particular data sample 216 corresponds to a binary value of 0. However, the equation of $d=r_1-r_2$ can be optimal when $r_1$ and $r_2$ have equal prior probabilities of occurrence and average envelope values at the sampling locations. If equal prior probabilities exist, but $r_1$ and $r_2$ do not have similar envelope values, the traditional decision rule (i.e., $d=r_1-r_2$) for envelope detectors cannot be used.

In one example, a threshold detector 238 of the mobile device 230 can detect a threshold for determining a corresponding value. In other words, the threshold detector 238 can calculate the threshold, and then compare the threshold to the difference signal (d). Based on whether the difference signal (d) is less than or greater than the threshold, a corresponding binary value can be determined. In one example, $r_1$ and $r_2$ can have different values at a particular sampling location ($t_1$). For example, the frequency of $r_1$ can be greater than zero and the frequency of $r_2$ can be zero. Similarly, at another sampling location ($t_2$), the frequency of $r_1$ can be zero and the frequency of $r_2$ can be greater than zero (but less than the frequency of $r_1$ at $t_1$). Thus, $r_1$ and $r_2$ have different values at the sampling instances $t_1$ and $t_2$. As a result, the difference signal (d) is then such that the value 0 is no longer an optimal decision threshold.

Therefore, the threshold detector 238 can determine that the threshold be calculated using the following:

$$threshold_d = \frac{mean_1 + mean_0}{2},$$

wherein $mean_1$ is a mean value of d at sampling time instances for which a correct demodulated output is "1" and $mean_0$ is a mean value of d at sampling time instances for which a correct demodulated output is "0". Each successive data sample 216 (or audio sample) can be assumed as a potential start of a packet. Sampling markers can be parked along a difference signal (d) with spacing equal to an assumed symbol length. For example, the sampling locations can be at $t_0$, $t_1$, $t_2$, etc. Using reference headers and footer sequences, the mean value of binary value 1 levels at sampled locations of the difference signal (d) can be computed. In addition, the mean value of binary level 0 levels at sampled locations of the difference signal (d) can be computed. Therefore, if $r_1-r_2=d<threshold_d$, then that particular data sample 216 corresponds to a binary value of "0". If $r_1-r_2=d>threshold_d$, then that particular data sample 216 corresponds to a binary value of "1".

As previously explained, the demodulator in the mobile device 230 can periodically select the data samples 216 from the modulated sensor data 214 according to a defined sampling rate. The demodulator can be preset to select one data sample 216 out of approximately every 7.056 data samples. The demodulator can determine whether the one data sample 216 represents a "0" or a "1" based on the $r_1$ and $r_2$ signals (and the difference signal) associated with the one data sample 216. If the mobile device 230 knows the amount of time between each binary value, then the mobile device 230 knows how often to take a reading (i.e., select a data sample). Depending on the $r_1$ and $r_2$ values for the reading in relation to the threshold, the mobile device 230 can determine whether the reading corresponds to a "0" or a "1".

However, that sampling rate can vary based on clock drift between the mobile device 230 and the wearable device 210. Due to variations on the clock rate on the microprocessor of the mobile device 230, the sampling rate can vary up or down by several percent. For example, one data sample can be selected approximately every 6.7 to 7.1 data samples. However, the sampling rate is to be precisely known at a given time in order to accurately decode the modulated sensor data 214. For example, the modulated sensor data 214 can be sent in packets to the mobile device 230. Each packet can have approximately 74 symbols (i.e., 74 0s and 1s). Due to the clock drift, the mobile device 230 can select the data sample 216 according to an inaccurate sampling rate. If the mobile device 230 samples a data sample 216 every 1 ms to determine a binary value for a given symbol, after 20 or 30 symbols, the sampling can drift into an adjacent symbol if the sampling rate is off by a few percent. For example, the sampling can drift into an earlier or later symbol. As a result, the mobile device 230 will sample the wrong symbol, thereby leading to inaccurate binary data. The inaccurate binary data (or demodulated digital sensor data) can lead to a calculation of an inaccurate heart rate for the user 250. Therefore, the sampling rate has to operate with less than 1% tolerance in order for the modulated sensor data 214 to be accurately demodulated.

In one configuration, a sampling rate estimator 240 of the mobile device 230 can use an adaptive down sampling technique to accurately set the sampling rate. Over time, the sampling rate estimator 240 can update the sampling rate due to clock drift. Since the clock drift can be negative or positive, the sampling rate estimator 240 can increment or decrement the sampling rate accordingly. In step 1, an initial down sampling rate can be set to one sample per 7.056 samples. In other words, one sample can be selected from every 7.056 samples of the modulated sensor data 214. In step 2, a tryout time "X" can be set to 0, a flag overflow parameter can be set to false, and a flag undertow parameter can be set to false. In step 3, signal samples collected from down sampling of the data packet can be obtained. In step 4, if the signal samples pass a cyclic redundancy code (CRC) check and header/tail bit tests, then the signal samples are deemed as valid decoded signals, and the adaptive down sampling technique goes to step 12. In step 12, a start of the next packet of data is sought, and the adaptive down sampling technique goes back to step 2. In step 4, if the signal samples do not pass the CRC check and the header/tail bit tests, then the signal samples are deemed as invalid decoded signals, and the adaptive down sampling technique resumes with step 5. In step 5, if the flag under flow parameter is false and X is positive, then X is changed to –X (or negative X). In step 6, if the flag overflow parameter is false and X is negative, then X is changed to –X+1. In step 7, one of the flag underflow parameter or the flag overflow parameter is true, but not both. If the flag underflow parameter is true, then X=X+1. If the flag overflow parameter is true, then X=X–1.

In step 8, the down sampling rate can be changed to "current rate+"X"×7.056). In step 9, if the current down sampling rate is larger than 7.056×1.035, then the flag overflow parameter can be set to true and X=–X+1. In step 10, if the current down sampling rate is larger than 7.056× 0.965, then the flag underflow parameter can be set to true and X=–X. In step 11, if both the flag overflow parameter and the flag underflow parameter are true, then detection failure is marked and the adaptive down sampling technique goes to step 12. Therefore, based on the adaptive down sampling technique, the decoder can guess clock drift values and attempts to successfully perform a decoding. When an acceptable signal is decoded, then the corresponding clock drift can be stored and used to decode the next packet of data. If the decoded signal is not acceptable, a nearby drift can be tried by incrementing by 1% and up to 3.5% until the decoded signal is acceptable.

A packet decoder 242 of the mobile device 230 can decode the sensor data 214 using the sampling rate and the threshold of $$\frac{mean_1 + mean_0}{2}.$$

In other words, the packet decoder 242 can periodically select data samples from the series of data samples 216 included in the sensor data 214. The packet decoder 242 can select the data samples in accordance with the sampling rate (e.g., one sample approximately every 7.056 samples or approximately every 11.84 ms), wherein the sampling rate can be adjusted in real time based on the clock drift. Each data sample that is selected can be associated with a particular sampling time instance. The packet decoder 242 can determine a discrete data value (i.e., a "0" or "1") for each selected data sample based on a comparison of the difference signal (d) between the first signal ($r_1$) and the second signal ($r_2$) associated with the selected data sample with respect to the threshold of $$\frac{mean_1 + mean_0}{2}.$$

The packet decoder 242 can determine whether header and footer sequences are decoded correctly, and if so, the data sequence can be decoded. In addition, the CRC can be decoded and verified. The packet decoder 242 can compute a packet score using a function that penalizes symbol samples that are close to a decision boundary. One example of the packet score can be a sum of squared symbol sample values within a packet. The decoded packet is then taken to be the sequence with a maximum score within each small window of the signal (i.e., the modulated sensor data 214). Therefore, the packet decoder 242 can successfully demodulate or decode the modulated sensor data 214, even when the sensor data 214 includes noise interference and clock drift is present between the mobile device 230 and the wearable device 210, by using adaptive down sampling. The packet decoder 214 can produce demodulated digital sensor data, which is then converted to heart rate information and displayed on the mobile device 230 to the user 250 via a display module 244.

Figure 3:
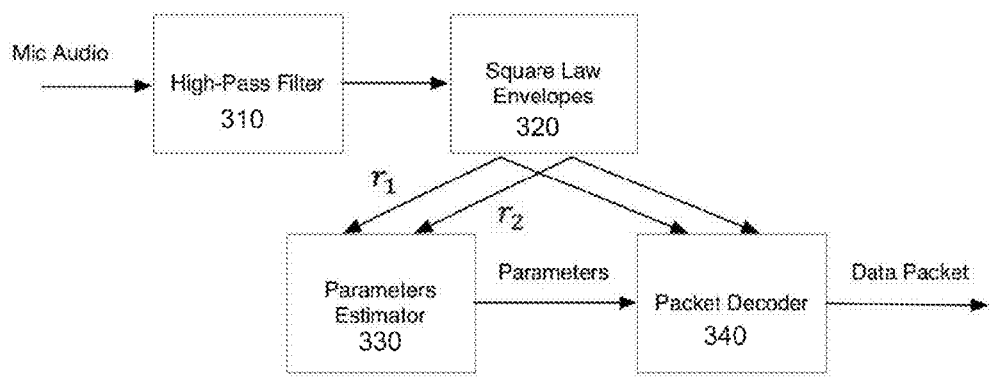
FIG. 3 illustrates a system and related operations for demodulating sensor data in accordance with an example.

FIG. 3 illustrates an exemplary system and related operations for demodulating sensor data. Microphone audio can be provided to a high-pass filter 310. The microphone audio can include modulated sensor data. The modulated sensor data can be modulated using two BFSK frequency tones (e.g., 12 kHz and 18 kHz). The high pass filter 310 can remove frequency components from the microphone audio other than those in between the two BFSK frequency tones. In other words, frequency components less than 12 kHz and greater than 18 kHz can be removed using the high pass filter 310. The high pass filter 310 can output a filtered signal, which can be provided to a square law envelopes processing unit 320. The square law envelopes processing unit 320 can output two signals ($r_1$ and $r_2$) from the filtered signal, wherein the two signals can be referred to as envelope signals.

The two envelope signals ($r_1$ and $r_2$) can be provided to a parameters estimator 330. The parameters estimator 330 can determine a sampling rate (as described above) that accounts for clock drift, as well as a decision threshold. The decision threshold can be calculated using a difference signal (d) between the first envelope signal ($r_1$) and the second envelope signal ($r_2$) at various sampling locations. The parameters estimator 330 can provide the parameters (e.g., the sampling rate and the decision threshold) to a packet decoder 340. The packet decoder 340 can use the parameters to demodulate or decode the modulated sensor data, thereby resulting in data packets.

Figure 4:
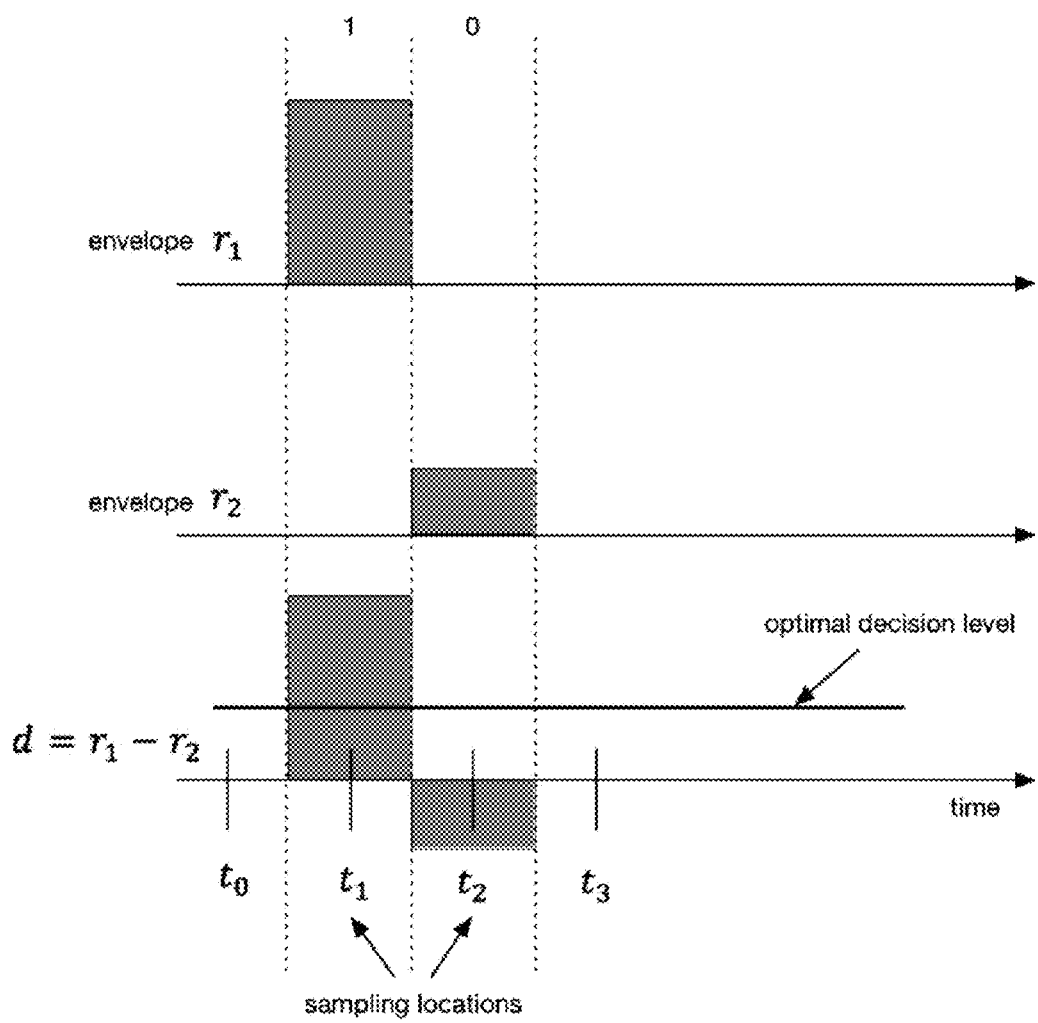
FIG. 4 illustrates sampling locations for selecting samples over a period of time in accordance with an example.

FIG. 4 illustrates exemplary sampling locations for selecting samples over a period of time. Modulated sensor data can be represented over a period of time. The modulated sensor data can include a plurality of data samples. Each data sample can correspond to approximately 12 kHz or 18 kHz. In addition, each data sample can be associated with a first envelope signal ($r_1$) and a second envelope signal ($r_2$). For a given data sample, when a frequency of $r_1$ is greater than zero, then a frequency of $r_2$ can be zero, and when the frequency of $r_1$ is zero, then a frequency of $r_2$ can be greater than zero. Either the first envelope signal ($r_1$) or the second envelope signal ($r_2$) can be associated with a certain frequency for a certain period of time (e.g., 7 samples) before the frequency changes. These periods of time can correspond to a discrete data value that is being communicated in the modulated sensor data. For example, as shown in FIG. 4, the period of time in which the frequency of $r_1$ is greater than zero can correspond to a binary value of "1". Similarly, the period of time in which the frequency of $r_2$ is greater than zero can correspond to a binary value of "0".

Sampling locations that correspond to a sampling rate can be selected. The sampling locations can be represented as $t_1$, $t_2$, $t_3$, etc. In one example, the sampling rate can be approximately every 7 samples. At each sampling location, a particular data sample (with corresponding envelope signals of $r_1$ and $r_2$) can be selected. A difference signal (d) between the first envelope signal ($r_1$) and the second envelope signal ($r_2$) can be calculated at each sampling location. The difference signal (d) can be compared to an optimal decision threshold. As shown in FIG. 4, at $t_1$, $r_1$ is greater than zero and $r_2$ is zero. Therefore, the difference signal (d) at $t_1$ is $r_1$. At $t_2$, $r_1$ is zero and $r_2$ is greater than zero, so the difference signal (d) at $t_2$ is $-r_2$. These difference signals can be compared to the optimal decision threshold, and based on the comparison, the selected sample at $t_1$, $t_2$, etc. can be associated with a binary value of "0" or a binary value of "1".

Figure 5:
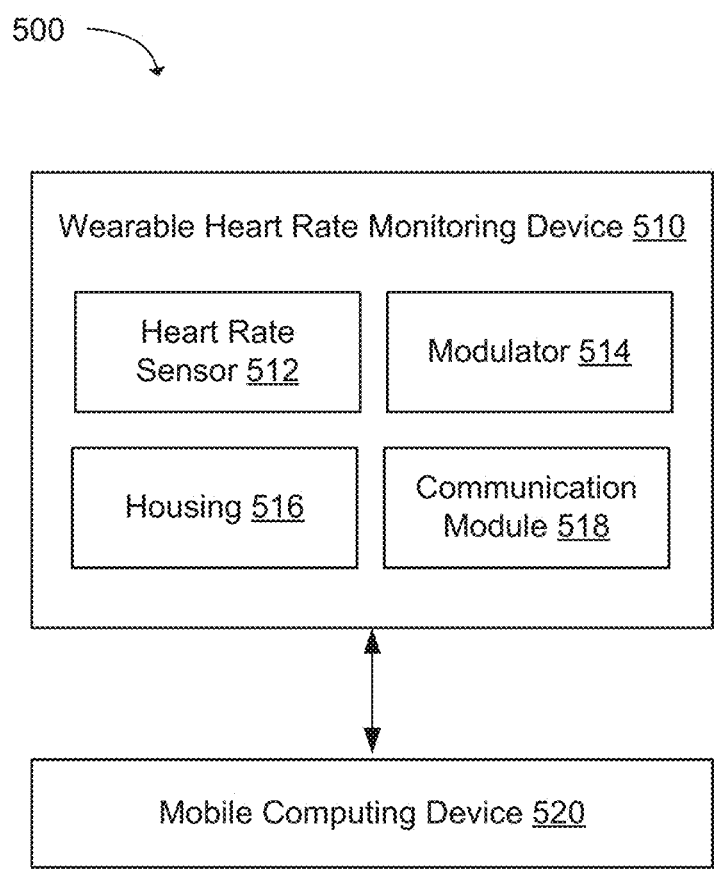
FIG. 5 depicts functionality of a mobile device operable for demodulating sensor data in accordance with an example.

Another example provides functionality 500 of a wearable heart rate monitoring device 510, as shown in the block diagram in FIG. 5. The wearable heart rate monitoring device 510 can include a heart rate sensor 512 operable to collect sensor data. The wearable heart rate monitoring device 510 can include a modulator 514 operable to generate a modulated signal that includes the sensor data. The wearable heart rate monitoring device 510 can include a housing 516 configured to engage a body feature or surface in a manner that allows for heart rate detection. The wearable heart rate monitoring device 510 can include a communication module 518 configured to transmit the sensor data in the modulated signal to a mobile computing device 520 via a wired connection that is power limited, wherein the mobile computing device 520 is configured to demodulate the modulated signal in order to extract the sensor data.

Figure 6:
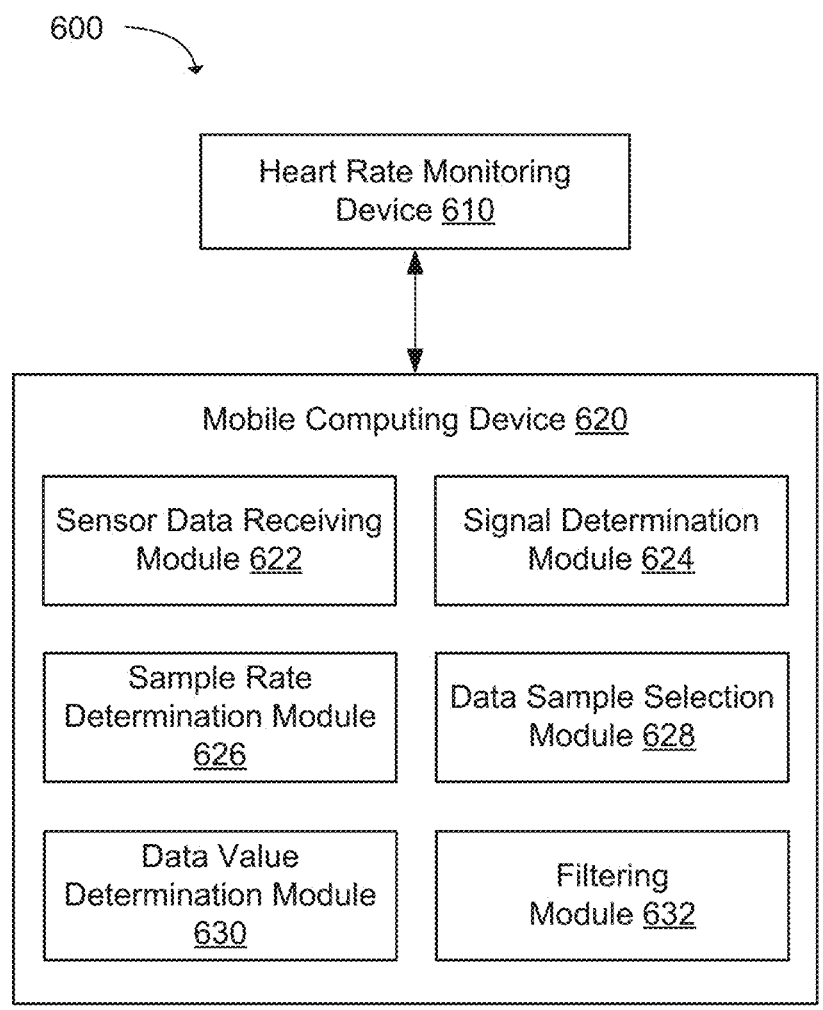
FIG. 6 depicts functionality of a system comprising a heart rate monitoring device and a mobile device in communication with the heart rate monitoring device via a wired connection in accordance with an example.

Another example provides functionality 600 of a system comprising a heart rate monitoring device 610 and a mobile computing device 620, as shown in the block diagram in FIG. 6. The mobile computing device 620 can be in communication with the heart rate monitoring device 610 via a wired connection. The mobile computing device 620 can include a sensor data receiving module 622 configured to receive sensor data from the heart rate monitoring device 610 via the wired connection, the sensor data including a series of data samples that are each modulated using one of two frequency tones. The mobile computing device 620 can include a signal determination module 624 configured to determine a first signal and a second signal associated with each data sample. The mobile computing device 620 can include a sample rate determination module 626 configured to determine a sampling rate at which to select data samples from the series of data samples. The mobile computing device 620 can include a data sample selection module 628 configured to select data samples from the series in accordance with the sampling rate, wherein each data sample is selected at a sampling time instance. The mobile computing device 620 can include a data value determination module 630 configured to determine a discrete data value for each data sample selected from the series of data samples, wherein discrete data values represent demodulated digital sensor data. The mobile computing device 620 can include a filtering module 632 configured to remove frequency components from the series of data samples in the sensor data other than the two frequency tones.

Figure 7:
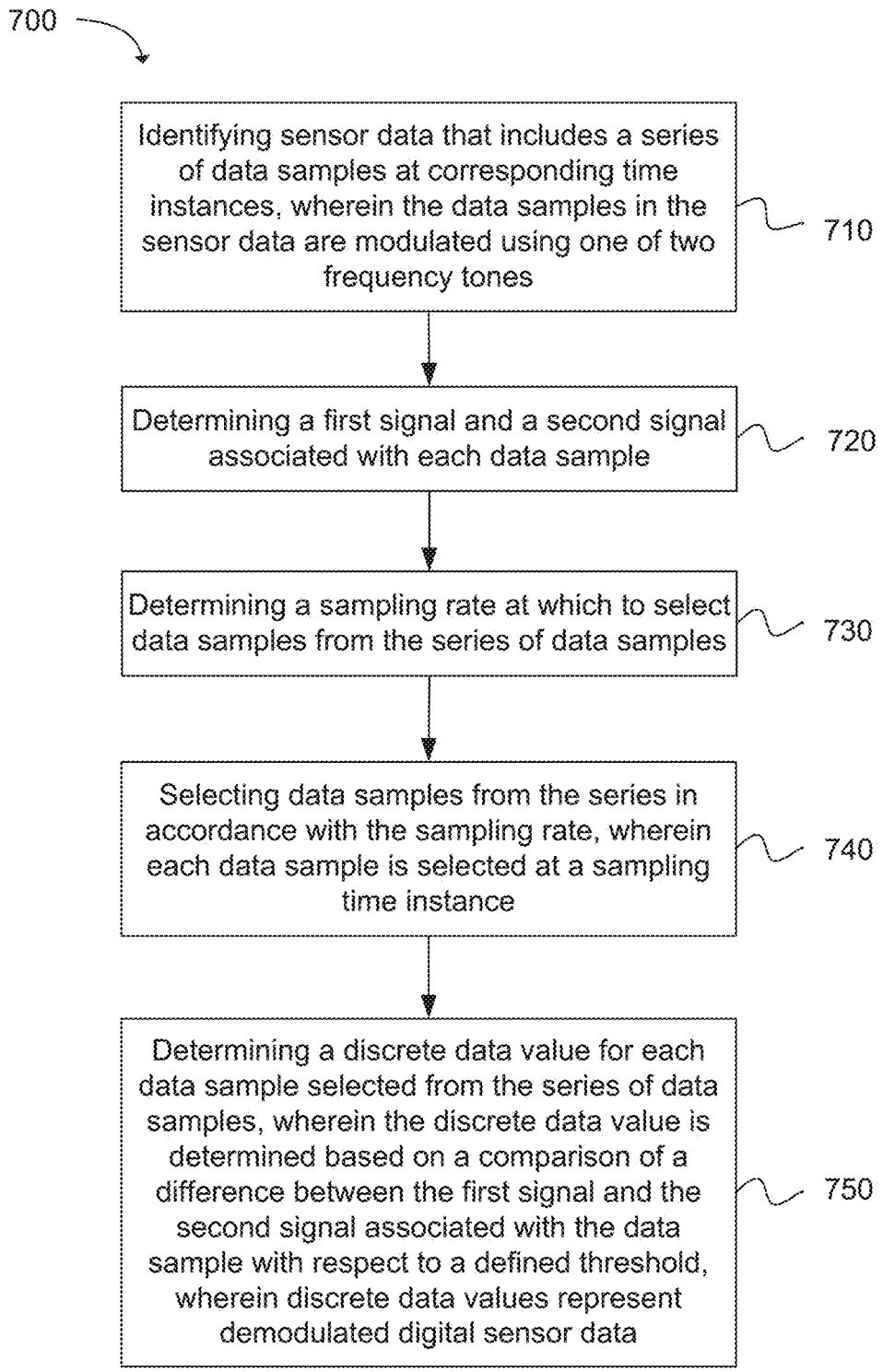
FIG. 7 depicts a flow chart of a method for demodulating sensor data collected from a wearable device in accordance with an example.

Another example provides a method 700 for generating notifications for a heart rate monitoring device, as shown in the flow chart in FIG. 7. The method can be executed as instructions on a machine, where the instructions are included on at least one computer readable medium or one non-transitory machine readable storage medium. The method can include the operation of identifying sensor data that includes a series of data samples at corresponding time instances, wherein the data samples in the sensor data are modulated using one of two frequency tones, as in block 710. The method can include the operation of determining a first signal and a second signal associated with each data sample, as in block 720. The method can include the operation of determining a sampling rate at which to select data samples from the series of data samples, as in block 730. The method can include the operation of selecting data samples from the series in accordance with the sampling rate, wherein each data sample is selected at a sampling time instance, as in block 740. The method can include the operation of determining a discrete data value for each data sample selected from the series of data samples, wherein the discrete data value is determined based on a comparison of a difference between the first signal and the second signal associated with the data sample with respect to a defined threshold, wherein discrete data values represent demodulated digital sensor data, as in block 750.

Figure 8:
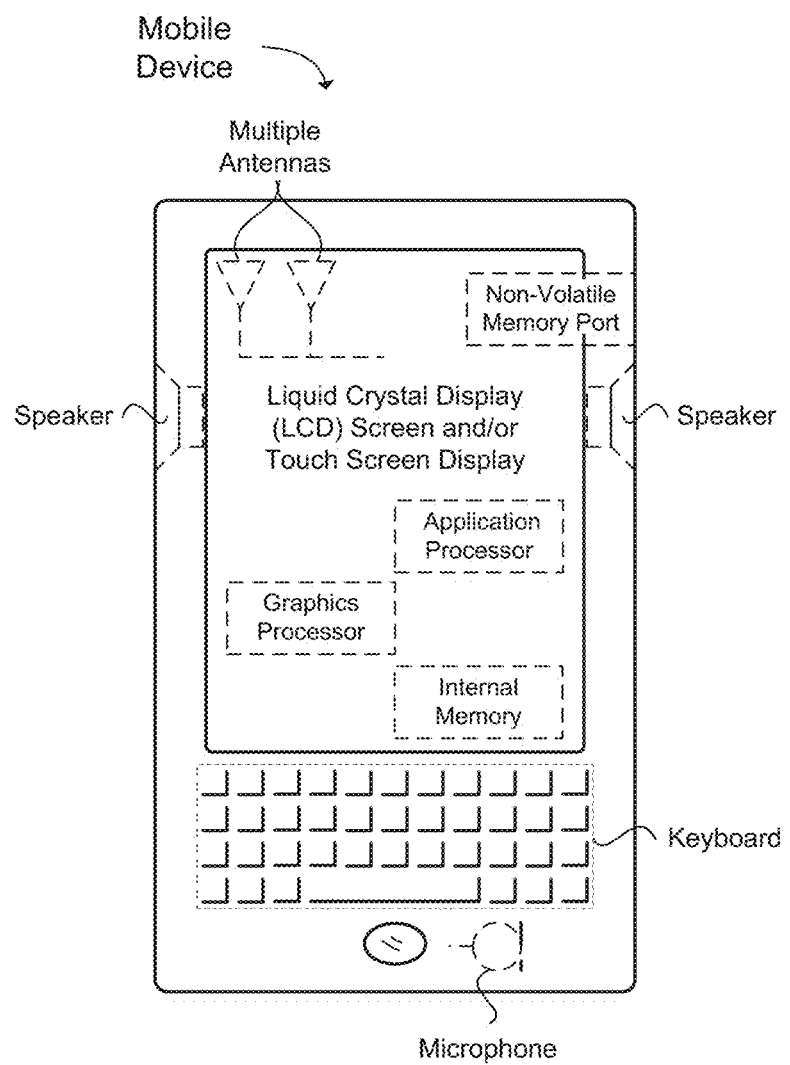
FIG. 8 illustrates a diagram of a wireless device in accordance with an example.

FIG. 8 provides an example illustration of a computing device, such as a mobile computing device. In one example, such a device can be a wearable device, a mobile wireless device, a mobile communication device, a tablet, a handset, or other type of wireless device. When a wireless device is used, it can include one or more antennas configured to communicate with a node, macro node, low power node (LPN), or, transmission station, such as a base station (BS), an evolved Node B (eNB), a baseband unit (BBU), a remote radio head (RRH), a remote radio equipment (RRE), a relay station (RS), a radio equipment (RE), or other type of wireless wide area network (WWAN) access point. The mobile computing device can be configured to communicate using at least one wireless communication standard including 3GPP LTE, WiMAX, High Speed Packet Access (HSPA), Bluetooth, and WiFi. The wireless device can communicate using separate antennas for each wireless communication standard or shared antennas for multiple wireless communication standards. The wireless device can communicate in a wireless local area network (WLAN), a wireless personal area network (WPAN), and/or a WWAN.

FIG. 8 also provides an illustration of a microphone and one or more speakers that can be used for audio input and output from the computing device. The display screen can be a liquid crystal display (LCD) screen, or other type of display screen such as an organic light emitting diode (OLED) display. The display screen can be configured as a touch screen. The touch screen can use capacitive, resistive, or another type of touch screen technology. An application processor and a graphics processor can be coupled to internal memory to provide processing and display capabilities. A non-volatile memory port can also be used to provide data input/output options to a user. The non-volatile memory port can also be used to expand the memory capabilities of the wireless device. A keyboard can be integrated with the wireless device or wirelessly connected to the wireless device to provide additional user input. A virtual keyboard can also be provided using the touch screen.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer (i.e. computing device), the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, solid state drive, or other medium for storing electronic data. The node and wireless device can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

It should be understood that many of the functional units described in this specification have been labeled as modules, in order to more particularly emphasize their implementation independence. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

While the forgoing examples are illustrative of various technology principles in one or more particular applications, it will be apparent to those of ordinary skill in the art that numerous modifications in form, usage and details of implementation can be made without the exercise of inventive faculty, and without departing from the principles and concepts of the invention.

In one exemplary invention embodiment there is provided a wearable heart rate monitoring device comprising:
- a sensor operable to collect sensor data;
- a modulator operable to generate a modulated signal that includes the sensor data;
- a housing configured to engage a body feature or surface of a user in a manner that allows for heart rate detection; and
- a communication module configured to transmit the sensor data in the modulated signal to a mobile computing device using a wired connection that is power-limited.

In one example, the modulator generates the modulated signal using binary frequency-shift keying (BPSK).

In one example, the power-limited wired connection includes a headphone line that connects the wearable heart rate monitoring device to the mobile computing device.

In one example, the wearable heart rate monitoring device further comprises a speaker connected to the headphone line.

In one example, the power-limited wired connection includes a microphone line that connects the wearable heart rate monitoring device to the mobile computing device.

In one example, the wearable heart rate monitoring device further comprises a microphone connected to the microphone line.

In one example, the wearable heart rate monitoring device further comprises at least one of: an accelerometer, a gyroscope, a proximity sensor, or a temperature sensor for collecting additional sensor data to be modulated by the modulator and communicated by the communication module to the mobile computing device using the power-limited wired connection.

In one example, the wearable heart rate monitoring device is an in-ear heart rate monitoring headphone.

In one example, the sensor data includes noise that exceeds a defined threshold, wherein the noise is caused by electrical coupling in the power-limited wired connection through which the sensor data is communicated to the mobile computing device.

In one example, the power-limited wired connection is configured to operate at a power below about 1 mW.

In one example, the sensor data comprises heart rate information.

In one example, the sensor data further comprises positioning information, movement information, proximity information, or temperature information.

In one example, the mobile computing device is configured to demodulate the modulated signal in order to extract the sensor data and output the sensor data to a user.

In one example, the mobile computing device is further configured to:
- receive the sensor data from the wearable heart rate monitoring device via the wired connection, wherein the sensor data includes a series of data samples that are each modulated using one of two frequency tones;
- determine a first signal and a second signal associated with each data sample;
- determine a sampling rate at which to select data samples from the series of data samples;
- select data samples from the series in accordance with the sampling rate, wherein each data sample is selected at a sampling time instance; and
- determine a discrete data value for each data sample selected from the series of data samples, wherein the discrete data value is determined based on a comparison of a difference between the first signal and the second signal associated with the data sample with respect to a defined threshold, wherein discrete data values represent demodulated digital sensor data.

In one example, the mobile computing device is further configured to:
- set the sampling rate to an initial value;
- collect data samples periodically based on the sampling rate;
- determine that the data samples do not pass at least one of a cyclic redundancy code (CRC) test, a header bit test or a tail bit test; and
- increment or decrement the initial value by a defined offset value until the data samples pass the CRC test, the header bit test or the tail bit test, wherein adjustment of the initial value mitigates sampling drift when selecting the data samples from the series of data samples.

In one example, the discrete data value that corresponds to a selected data sample is "0" when the difference (d) between the first signal (r1) and the second signal (r2) is less than the defined threshold, or the discrete data value that corresponds to the selected data sample is "1" when the difference (d) between the first signal (r1) and the second signal (r2) is greater than the defined threshold, wherein the defined threshold is represented as:

$$threshold_d = \frac{mean_1 + mean_0}{2}$$

wherein $mean_1$ is a mean value of (d) at sampling time instances for which a correct demodulated output is "1" and $mean_0$ is a mean value of (d) at sampling time instances for which a correct demodulated output is "0".

In one example, a single data sample is selected from the series of data samples approximately every 7 data samples or approximately every 12 milliseconds (ms) in accordance with the sampling rate, wherein the approximately 7 data samples or 12 ms is adjusted based on sampling drift.

In one example, the mobile computing device is further configured to:
- modify the sampling rate at which to select the data samples in order to account for sampling drift, wherein the sampling drift occurs when a clock in the wearable device drifts from a clock in the mobile computing device; and
- apply the modified sampling rate when selecting subsequent data samples from the series of data samples.

In one example, the first signal of the data sample has a frequency greater than zero when the second signal of the data sample has a frequency that is substantially zero, or the first signal of the data sample has a frequency that is substantially zero when the second signal of the data sample has a frequency greater than zero.

In one example, the mobile computing device is further configured to:
remove frequency components from the series of data samples in the sensor data other than the two frequency tones via a high pass filter.

In one example, the mobile computing device is further configured to:
remove frequency components from the series of data samples in the sensor data other than the two frequency tones via a finite impulse response (FIR) filter with a cutoff frequency in a range of approximately 9-10 kilohertz (kHz).

In one example, the two frequency tones used to modulate the data samples in the sensor data include a first frequency tone of approximately 12 kilohertz (kHz) and a second frequency tone of approximately 18 kHz.

In one example, the first signal (r1) of the data sample is represented by $$r_1 = \sqrt{\cos(2\pi f_c t)^2 + \sin(2\pi f_c t)^2}$$

wherein fc is a signal frequency and t is a period of time.

In one example, the second signal (r2) of the data sample is represented by $$r_2 = \sqrt{\cos(2\pi (f_c + \Delta F)t)^2 + \sin(2\pi (f_c + \Delta F)t)^2}$$

wherein fc is a signal frequency, $\Delta F$ is a frequency offset, and t is a period of time.

In one example, the first signal and the second signal associated with each data sample are envelope signals that are identified using an envelope detector.

In one example, the first signal and the second signal associated with each data sample are identified via square law processing.

In an exemplary invention embodiment there is provided, a heart rate monitoring system, comprising:
a wearable heart rate monitoring device as recited in claim 1; and
a mobile computing device in communication with the heart rate monitoring device via a power-limited wired connection, the mobile computing device comprising:
a processor;
a memory device including a data store to store a plurality of data and instructions that, when executed by the processor, cause the processor to execute:
a sensor data receiving module configured to receive sensor data from the heart rate monitoring device via the power-limited wired connection, the sensor data including a series of data samples that are each modulated using one of two frequency tones;
a signal determination module configured to determine a first signal and a second signal associated with each data sample;
a sample rate determination module configured to determine a sampling rate at which to select data samples from the series of data samples;
a data sample selection module configured to select data samples from the series in accordance with the sampling rate, wherein each data sample is selected at a sampling time instance; and
a data value determination module configured to determine a discrete data value for each data sample selected from the series of data samples, wherein discrete data values represent demodulated digital sensor data.

In one example, the sample rate determination module is further configured to:
set the sampling rate to an initial value;
collect data samples based on the sampling rate;
determine that the data samples do not pass at least one of a cyclic redundancy code (CRC) test, a header bit test or a tail bit test; and
increment or decrement the initial value by a defined offset value until the data samples pass the CRC test, the header bit test or the tail bit test, wherein adjustment of the initial value mitigates sampling drift when selecting the data samples from the series of data samples.

In one example, the data value determination module is further configured to determine that the discrete data value for the data sample is "0" when a difference between the first signal (r1) and the second signal (r2) associated with the data sample is less than a defined threshold.

In one example, the data value determination module is further configured to determine that the discrete data value for the data sample is "1" when a difference between the first signal (r1) and the second signal (r2) associated with the data sample is greater than a defined threshold.

In one example, the sensor data includes noise that exceeds a defined threshold, wherein the noise is caused by electrical coupling in a microphone line that connects the mobile computing device and the heart rate monitoring device.

In one example, the system further comprises a filtering module configured to remove frequency components from the series of data samples in the sensor data other than the two frequency tones.

In one example, the signal determination module is further configured to determine the first signal and the second signal via square law processing, wherein the first signal and the second signal are envelope signals.

In one example, the first signal (r1) of the data sample is represented by $$r_1 = \sqrt{\cos(2\pi f_c t)^2 + \sin(2\pi f_c t)^2}$$

wherein fc is a signal frequency and t is a period of time.

In one example, the second signal (r2) of the data sample is represented by $$r_2 = \sqrt{\cos(2\pi (f_c + \Delta F)t)^2 + \sin(2\pi (f_c + \Delta F)t)^2}$$

wherein fc is a signal frequency, $\Delta F$ is a frequency offset, and t is a period of time.

In one example, the demodulated digital sensor data includes heart rate information.

In one exemplary invention embodiment, there is provided a method of obtaining heart rate data from a subject comprising:
under control of one or more computer systems configured with executable instructions:
collecting sensor data from the subject with a heart rate sensor;
modulating the sensor data with a data modulator to produce a signal that includes the sensor data;
communicating the sensor data to a mobile computing device having one or more processors via a power-limited wired connection;
demodulating the sensor data from the signal with a data demodulator in the mobile computing device; and
outputting the sensor data to a user.

In one example the heart rate sensor is a wearable heart rate sensor device comprising:
a sensor operable to collect sensor data;

a modulator operable to generate a modulated signal that includes the sensor data;

a housing configured to engage a body feature or surface of a user in a manner that allows for heart rate detection; and a communication module configured to transmit the sensor data in the modulated signal to the mobile computing device using the power-limited wired connection.

In one example, modulating the sensor data includes modulating a series of data samples using one of two frequency tones and producing a first signal and a second signal for each data sample.

In one example, the first signal of the data sample has a frequency greater than zero when the second signal of the data sample has a frequency that is substantially zero; or the first signal of the data sample has a frequency that is substantially zero when the second signal of the data sample has a frequency greater than zero.

In one example, the two frequency tones used to modulate the data samples in the sensor data include a first frequency tone of approximately 12 kilohertz (kHz) and a second frequency tone of approximately 18 kHz.

In one example, the first signal (r1) of the data sample is represented by $$r_1 = \sqrt{\cos(2\pi f_c t)^2 + \sin(2\pi f_c t)^2}$$

wherein fc is a signal frequency and t is a period of time.

In one example, the second signal (r2) of the data sample is represented by $$r_2 = \sqrt{\cos(2\pi (f_c + \Delta F) t)^2 + \sin(2\pi (f_c + \Delta F) t)^2}$$

wherein fc is a signal frequency, $\Delta F$ is a frequency offset, and t is a period of time.

In one example, demodulating further comprises:

identifying sensor data that includes a series of data samples at corresponding time instances using the one or more processors of the mobile computing device;

determining a first signal and a second signal associated with each data sample, using the one or more processors of the mobile computing device;

determining a sampling rate at which to select data samples from the series of data samples, using the one or more processors of the mobile computing device;

selecting data samples from the series in accordance with the sampling rate, wherein each data sample is selected at a sampling time instance, using the one or more processors of the mobile computing device; and determining a discrete data value for each data sample selected from the series of data samples, wherein the discrete data value is determined based on a comparison of a difference between the first signal and the second signal associated with the data sample with respect to a defined threshold, wherein discrete data values represent demodulated digital sensor data, using the one or more processors of the mobile computing device.

In one example, determining the sampling rate further comprises:

setting the sampling rate to an initial value;

collecting data samples based on the sampling rate;

determining that the data samples do not pass at least one of a cyclic redundancy code (CRC) test, a header bit test or a tail bit test; and incrementing or decrementing the initial value by a defined offset value until the data samples pass the CRC test, the header bit test and the tail bit test, wherein the initial value is modified in order to mitigate sampling drift when selecting the data samples from the series of data samples.

In one example, the discrete data value that corresponds to the selected data sample is "0" when the difference (d) between the first signal (r1) and the second signal (r2) is less than the defined threshold; or the discrete data value that corresponds to the selected data sample is "1" when the difference (d) between the first signal (r1) and the second signal (r2) is greater than the defined threshold, wherein the defined threshold is represented as:

$$threshold_d = \frac{mean_1 + mean_0}{2}$$

wherein mean1 is a mean value of d at sampling time instances for which a correct demodulated output is "1" and mean0 is a mean value of d at sampling time instances for which a correct demodulated output is "0".

In one example, a single data sample is selected from the series of data samples approximately every 7 data samples or approximately every 12 milliseconds (ms) in accordance with the sampling rate, wherein the approximately 7 data samples or 12 ms is adjusted based on sampling drift.

In one example, the method further comprises:

modifying the sampling rate at which to select the data samples in order to account for sampling drift, wherein the sampling drift occurs when a clock in the wearable device drifts from a clock in a mobile computing device demodulating the sensor data; and applying the modified sampling rate when selecting subsequent data samples from the series of data samples.

In one example, the method further comprises removing frequency components from the sensor data other than the two frequency tones via a high pass filter.

In one example, the method further comprises removing frequency components from the sensor data other than the two frequency tones via a finite impulse response (FIR) filter with a cutoff frequency in a range of approximately 9-10 kilohertz (kHz).

In one example, the first signal and the second signal for each data sample are envelope signals that are identified using an envelope detector.

In one example, the sensor data is demodulated at a mobile computing device that is connected to the wearable device via a microphone line.

In one example, the sensor data is output to a user visually.

In one example, the sensor data is output to a user audibly.

While the forgoing examples are illustrative of the specific embodiments in one or more particular applications, it will be apparent to those of ordinary skill in the art that numerous modifications in form, usage and details of implementation can be made without departing from the principles and concepts articulated herein.

What is claimed is:

1. A wearable heart rate monitoring device comprising:
an earbud housing configured to engage an ear of a user;
a headphone disposed in the earbud hosing, the headphone operable to output soundwaves to the ear of the user based on audio signals;
a wired connection coupled to the headphone, the wired connection operable to transmit the audio signals to the headphone, wherein the wired connection is power-limited;
a sensor disposed in the earbud housing, the sensor operable to collect sensor data including heart rate information from the ear of the user;

a modulator disposed in the earbud housing and coupled to the sensor, the modulator operable to generate a modulated signal using binary frequency-shift keying (BFSK) that includes the heart rate information; and a communication module disposed in the earbud housing and coupled to the modulator and the wired connection, the communication module operable to transmit the heart rate information in the modulated signal to a mobile computing device using the wired connection that is power-limited.

2. The wearable heart rate monitoring device of claim 1, wherein the wired connection of the earbud includes a speaker line.

3. The wearable heart rate monitoring device of claim 1, wherein the wired connection of the earbud includes a microphone line.

4. The wearable heart rate monitoring device of claim 1, wherein the sensor data includes noise that exceeds a defined threshold, wherein the noise is caused by electrical coupling of audio signals in the wired connection of the earbud through which the heart rate information in the modulated signal is communicated to the mobile computing device.

5. The wearable heart rate monitoring device of claim 1, wherein the power-limited wired connection is configured to operate at a power below about 1 mW.

6. The wearable heart rate monitor device of claim 1, further comprising the mobile computing device operable to demodulate the modulated signal in order to extract the heart rate information and output the heart rate information to the user.

7. The wearable heart rate monitoring device of claim 6, wherein the mobile computing device is further operable to:
receive the modulated signal from the wearable heart rate monitoring device via the wired connection, wherein the modulated signal includes a series of data samples that are each modulated using one of two frequency tones;
determine a first signal and a second signal associated with each data sample;
determine a sampling rate at which to select data samples from the series of data samples;
select data samples from the series in accordance with the sampling rate, wherein each data sample is selected at a sampling time instance; and
determine a discrete data value for each data sample selected from the series of data samples, wherein the discrete data value is determined based on a comparison of a difference between the first signal and the second signal associated with the data sample with respect to a defined threshold, wherein discrete data values represent demodulated heart rate information.

8. The wearable heart rate monitoring device of claim 7, wherein:
the discrete data value that corresponds to a selected data sample is "0" when the difference (d) between the first signal (r1) and the second signal (r2) is less than the defined threshold; or
the discrete data value that corresponds to the selected data sample is "1" when the difference (d) between the first signal (r1) and the second signal (r2) is greater than the defined threshold,
wherein the defined threshold is represented as:

$$threshold_d = \frac{mean_1 + mean_0}{2}$$

wherein mean1 is a mean value of (d) at sampling time instances for which a correct demodulated output is "1" and mean0 is a mean value of (d) at sampling time instances for which a correct demodulated output is "0".

9. The wearable heart rate monitoring device of claim 7, wherein a single data sample is selected from the series of data samples approximately every 7 data samples or approximately every 12 milliseconds (ms) in accordance with the sampling rate, wherein the approximately 7 data samples or 12 ms is adjusted based on sampling drift.

10. The wearable heart rate monitoring device of claim 7, wherein:
the first signal of the data sample has a frequency greater than zero when the second signal of the data sample has a frequency that is substantially zero; or
the first signal of the data sample has a frequency that is substantially zero when the second signal of the data sample has a frequency greater than zero.

11. The wearable heart rate monitoring device of claim 7, wherein the two frequency tones used to modulate the data samples in the sensor data include a first frequency tone of approximately 12 kilohertz (kHz) and a second frequency tone of approximately 18 kHz.

12. The wearable heart rate monitoring device of claim 7, wherein the first signal (r1) of the data sample is represented by $r_1 = \sqrt{\cos(2\pi f_c t)^2 + \sin(2\pi f_c t)^2}$ wherein fc is a signal frequency and t is a period of time.

13. The wearable heart rate monitoring device of claim 7, wherein the second signal (r2) of the data sample is represented by $r_2 = \sqrt{\cos(2\pi(f_c + \Delta F)t)^2 + \sin(2\pi(f_c + \Delta F)t)^2}$ wherein fc is a signal frequency, ΔF is a frequency offset, and t is a period of time.

14. A heart rate monitoring system, comprising:
a wearable heart rate monitoring device as recited in claim 1; and
a mobile computing device in communication with the heart rate monitoring device via the wired connection, the mobile computing device comprising:
a processor;
a memory device including a data store to store a plurality of data and instructions that, when executed by the processor, cause the processor to execute:
a sensor data receiving module configured to receive the BSK modulated signal from the heart rate monitoring device via the wired connection of the earbud, the BSK modulated signal including a series of data samples that are each modulated using one of two frequency tones;
a signal determination module configured to determine a first signal and a second signal associated with each data sample;
a sample rate determination module configured to determine a sampling rate at which to select data samples from the series of data samples;
a data sample selection module configured to select data samples from the series in accordance with the sampling rate, wherein each data sample is selected at a sampling time instance; and
a data value determination module configured to determine a discrete data value for each data sample selected from the series of data samples, wherein discrete data values represent demodulated heart rate information.

15. The system of claim 14, wherein the sample rate determination module is further configured to:
set the sampling rate to an initial value;
collect data samples based on the sampling rate;

determine that the data samples do not pass at least one of a cyclic redundancy code (CRC) test, a header bit test or a tail bit test; and increment or decrement the initial value by a defined offset value until the data samples pass the CRC test, the header bit test or the tail bit test, wherein adjustment of the initial value mitigates sampling drift when selecting the data samples from the series of data samples.

16. The system of claim 14, further comprising a filtering module configured to remove frequency components from the series of data samples in the modulated signal other than the two frequency tones.

17. The system of claim 14, wherein the signal determination module is further configured to determine the first signal and the second signal via square law processing, wherein the first signal and the second signal are envelope signals.

18. A wearable device comprising:
a housing configured to engage an ear canal of a user;
a headphone, disposed in the housing;
an audio line configured to conduct an audio signal for the headphone;
a heart rate sensor, disposed in the housing, to sense heart rate information at the ear canal of the user;
a modulation module, disposed in the housing and communicatively coupled to the heart rate sensor, to encode the heart rate information in a modulated signal using binary frequency-shift keying (BF SK); and
a communication module, disposed in the housing and communicatively coupled between the modulation module and the audio line, to transmit the modulated signal on the audio line.

19. The wearable device of claim 18, further including:
a microphone, communicatively coupled to the audio line to transmit a microphone signal; and
a switch to selective transmit one or the microphone signal and the modulated signal.

* * * * *